(12) United States Patent  (10) Patent No.: US 7,502,174 B2
Jensen et al.  (45) Date of Patent: Mar. 10, 2009

(54) SYSTEM AND METHOD FOR IMAGING

(75) Inventors: Vernon Thomas Jensen, Draper, UT (US); Stephen Johnson Lomnes, Philadelphia, PA (US)

(73) Assignee: General Electric Company, Schenectady, NY (US)

( * ) Notice: Subject to any disclaimer, the term of this patent is extended or adjusted under 35 U.S.C. 154(b) by 97 days.

(21) Appl. No.: 11/563,002

(22) Filed: Nov. 23, 2006

(65) Prior Publication Data

US 2008/0122936 A1 May 29, 2008

(51) Int. Cl.
*G02B 15/14* (2006.01)
*G03B 29/00* (2006.01)

(52) U.S. Cl. .......................... 359/694; 396/14; 396/18; 396/155; 348/77; 348/370; 600/476

(58) Field of Classification Search ............. 396/14–18, 396/155, 419–428; 348/14.05, 77, 211.99, 348/370–371; 600/476
See application file for complete search history.

(56) References Cited

U.S. PATENT DOCUMENTS

2002/0015296 A1* 2/2002 Howell et al. .................. 362/11

* cited by examiner

*Primary Examiner*—Jessica T Stultz
*Assistant Examiner*—Mahidere S Sahle
(74) *Attorney, Agent, or Firm*—Peter Vogel, Esq.; Bill Baxter, Esq.; Michael G. Smith, Esq.

(57) ABSTRACT

A system provides a multi-axis translation and orientation capability for optical imaging. The system includes an optical imaging apparatus providing a signal representing a digitized image, and a mechanical frame. The frame includes a first set of articulations capable of independently translating the optical imaging apparatus in multiple linear directions. The system also includes a second set of articulations formed as joints providing at least three independent degrees of rotation of the optical imaging apparatus. The system also provides an opening configured to permit the frame to be postured about a patient such that an isocenter corresponds to a region of interest of the patient, and includes an illumination source attached to the frame and configured to direct illumination towards the isocenter. The system also comprises a camera system co-located with the illumination source and having a focal plane at the isocenter.

14 Claims, 6 Drawing Sheets

SYSTEM AND METHOD FOR IMAGING

FIELD OF THE DISCLOSURE

This disclosure relates generally to imaging technology, and in particular to a system and method for positioning imaging equipment relative to an isocenter or locus associated with a region of interest.

BACKGROUND

Many medical diagnostic, surgical and interventional procedures rely on imaging tools to provide information descriptive of status of visually perceived representations of portions or organs of a patient. In part as a result of increasing sophistication of medical tools in general, and imaging apparatus in particular, more types of imaging devices are being adapted for application in the context of surgical procedures.

In many instances, medical tools capable of rendering images of organs or tissues have found great utility and have been adapted to facilitate types of surgery. These find application in many situations, and are very useful in situations where the surgeon cannot directly see the operating site, or when the features of interest are not amenable to direct visual inspection, or to enable comparison of a present image with other image data, among other instances. These applications have resulted in development of a broad variety of tools, including x-ray, CT and fluoroscopic visualizing aids, and many different types of optical imaging devices.

In turn, such applications frequently benefit when the imaging tool is mobile or portable, easily positioned to achieve a desired position and to hold the desired position, may be readily adjusted about an isocenter or patient-centric locus, may include capability for machine-driven positioning, provides a stable platform, and presents numerous other aspects somewhat unique to the operating room environment. These include need to be compliant with safety and regulatory requirements for medical imaging equipment, and to satisfy sterility requirements within the operating room, such as control of air borne particulates, compatibility with draping, and constraints relating to fluid containment and cleaning.

Accordingly, the resultant support systems for such visualization equipment include significant mechanical considerations in order to facilitate the required degrees of freedom in articulation and transportation. A suitable footprint and acceptable mobility, each adapted to the operating room environment, are important aspects. There may be need to provide capability for self-contained propulsion, and for onboard control and visualization aspects, together with suitable electrical power and signal sharing capabilities. Use of a modular 'drop-in' shielded electronics cabinet allows exchange or modification of control and/or signal processing apparatus. Other environmental apparatus, such as chillers, may be needed and may be directed to the imaging apparatus itself. Design, manufacture, operation and maintenance are all capable of some degree of benefit when similar requirements may be addressed using similarly-developed and operated equipment, to some extent.

In many imaging applications, pixelated detectors are increasingly employed to realize electronic digital representations of image data. In turn, digital techniques provide great imaging flexibility, such as, for example, overlay or direct comparison, on the fly, of various aspects and views from various times. For example, pre-surgery images can be available, in real time, in the operating room scenario, for comparison to images reflective of the present status of the same tissues. Many other types of special-purpose enhancements are now also possible. In some instances, imaging aids, such as contrast-enhancing agents, are introduced into the subject or patient to aid in increasing available data content from the imaging technique or techniques being employed.

Increasing sophistication of these imaging and visualization apparatus also result in significant cost, not only develop these devices, but also to acquire them, to train operators in using them, and service technicians to maintain them, and in educating physicians to be familiar with their capabilities and benefits. As a result, a significant investment is involved with respect to each such tool.

The advent of digital imaging technologies resulted in a large number of new medical applications and usages for imaging tools. Digital images are made up of pixels, and these images are generally visualized by assigning each pixel a numerical value corresponding to a color or a shade of gray, and then displaying that assigned representation in the corresponding position for that pixel on a graphical display. A digital image can be adjusted by varying the numerical values of each pixel, for example by forming each pixel as a weighted combination of images formed at different times, or formed from illumination from different spectral components or by combining images including light-emitting, shadow-graphic, and reflected image data. The raw image data is manipulated by software using algorithms and mathematical computations to optimize the image. These types of images, alone or in combination with other data, provide useful tools for improving medical procedures.

For the reasons stated above, and for other reasons discussed below, which will become apparent to those skilled in the art upon reading and understanding the present disclosure, there are needs in the art to provide more highly automated image computation engines and protocols for application and usage of such capabilities, in order to streamline gathering of information in support of increasingly stringent and exacting performance and economic standards in settings such as medical imaging.

BRIEF DESCRIPTION

The above-mentioned shortcomings, disadvantages and problems are addressed herein, which will be understood by reading and studying the following disclosure.

In one aspect, a system provides a multi-axis translation and orientation capability for optical imaging. The system includes an optical imaging apparatus providing a signal representing a digitized image and a frame. The frame includes a first set of articulations capable of independently translating the optical imaging apparatus in multiple linear directions. The system also includes a second set of articulations formed as joints providing at least three independent degrees of rotation of the optical imaging apparatus. The system also provides an opening configured to permit the frame to be postured about a patient such that an isocenter corresponds to a region of interest of the patient, and an illumination source attached to the frame and configured to direct illumination towards the isocenter. The system also comprises an image detection apparatus co-located with the illumination source and having a focal plane at the isocenter. The image detection apparatus provides the signal, and the signal includes electronic information representing a pixelated optical image of the region of interest.

In another aspect, a camera support includes a rigid member, and an illumination source rotatably mounted on the rigid member. A camera system is mounted on the rigid member with the illumination source and is coupled thereto. The camera system is responsive to illumination associated with the illumination source and has a focal plane. A group of guides are coupled to the rigid member, the guides having mutually orthogonal axes of motion. At least one of the guides includes a computer-controllable motor drive for lifting the rigid member. A group of joints each contribute a degree of freedom of rotation to the rigid member. A basal member is coupled to the rigid member via the group of guides and the group joints, and the rigid member is thus cantilevered. The group of guides and the group of joints cooperate to adjust a position of the camera system to cause the focal plane to coincide with a region of interest, and to facilitate motion of the camera system while maintaining the focal plane in coincidence with the region of interest.

In a further aspect, a mobile optical imaging system includes an arcuate supporting member and an optical imaging apparatus coupled to one end of the arcuate supporting member. The optical imaging apparatus includes an illumination source and a camera system. The camera system provides a digital signal representing an image. A first counterweight is coupled to an end of the arcuate supporting member distal from the one end such that the first counterweight is opposed to the optical imaging apparatus. A basal member provides a second counterweight for cantilevering the arcuate support member. The basal member also includes a self-contained power supply and has motorized propulsion capabilities. The arcuate member is slidably coupled to the basal member to permit rotation of the optical imaging apparatus and the first counterweight about an isocenter coincident with a focal plane of the optical imaging assembly. A data conditioning module is provided that is capable of processing the digital signal to provide a modified signal representing a desired image type. A display is coupled to the data conditioning module. The display is configured to provide an optical image based on the modified signal.

Systems, processes, and computer-readable media of varying scope are described herein. In addition to the aspects and advantages described in this summary, further aspects and advantages will become apparent by reference to the drawings and by reading the following detailed description.

DETAILED DESCRIPTION

Figure 1:
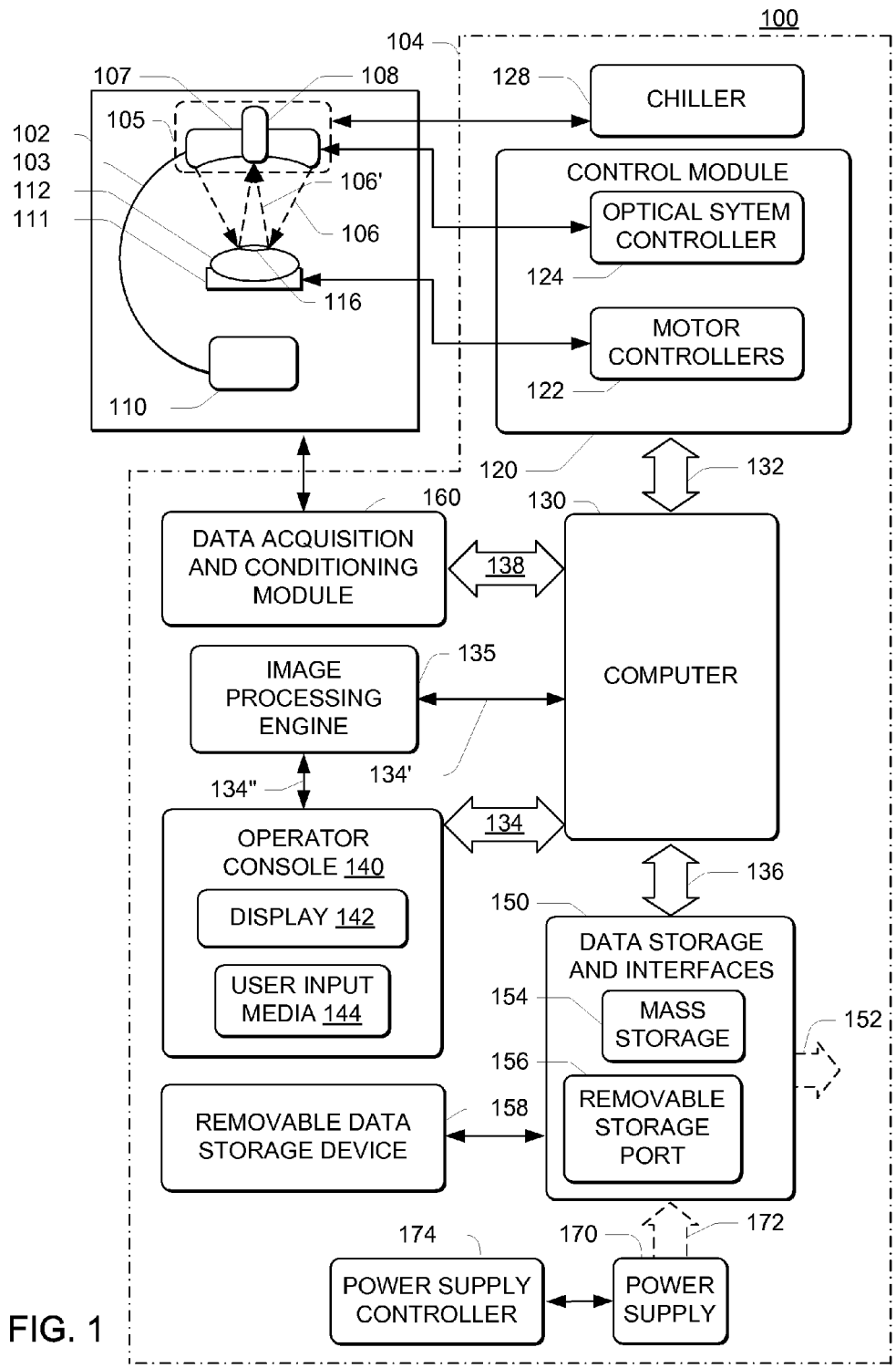
FIG. 1 is a block diagram of an overview of a system configured to improve the display of images from an imaging apparatus.

In the following detailed description, reference is made to the accompanying drawings that form a part hereof, and in which are shown, by way of illustration, specific embodiments that may be practiced. These embodiments are described in sufficient detail to enable those skilled in the art to practice the embodiments, and it is to be understood that other embodiments may be utilized, and that logical, mechanical, electrical and other changes may be made, without departing from the scope of the embodiments.

The term "optical imaging system" as used herein may include one or more cameras or camera systems, with computers, electronics, software and an optional illumination system. The term "illumination system" as used herein refers to a source of photons that may be provided by incandescent, LED, or laser based apparatus whose light output may be spectrally controlled by interference, holographic, and absorptive, or tunable filters, whose intensity may be time-varying and modified by the electronics and/or computer controls. The terms "camera" and "camera system" as used herein refer to a collection of one or more detectors configured with interference, holographic, absorptive, dichroic, or tunable filters; mirrors; and lenses that capture images which may be under the control of the computer and/or electronics that may be optionally synchronized to an illumination system.

The term "optical Imaging" as used herein refers to an imaging modality that may include imaging based on illumination in the visible light spectrum, and/or which may comprise image information derived from illumination in the ultraviolet, visible and infrared light spectral regions, for enhancing intra-operative visualization and characterization of tissues through their endogenous optical properties, or bioluminescence or chemiluminesence (i.e., not necessarily involving any explicit external light source), and/or with various contrast/fluorescent agents or thermography. This is an arena which is currently the subject of many research projects being conducted at various institutions and corporations, often in cooperation with clinical partners.

As used herein, the term "arcuate" refers to a shape that may comprise a portion or all of an ellipse or circle. As used herein, the term "illumination" is defined to refer to photons which do not necessarily correspond to light visible to humans. Ranges of parameter values described herein are understood to include all subranges falling therewithin. The following detailed description is, therefore, not to be taken in a limiting sense.

The detailed description is divided into five sections. In the first section, a system level overview is provided. In the second section, examples of mobile optical imaging system configurations are described. In the third section, an optical imaging system useful in the context of the preceding sections is discussed. The fourth section discloses hardware and an operating environment, in conjunction with which embodiments may be practiced. The fifth section provides a conclusion which reviews aspects of the subject matter described in the preceding four segments of the detailed description. A technical effect of the systems and processes described herein includes provision of optical images in situ in operating room environments and finding application in medical technologies.

I. System Overview

FIG. 1 is a simplified diagram of an overview of an imaging system 100 that is configured to improve display of images from one or more imaging tools. The imaging system 100 includes a mount aspect 102 that may comprise a gantry, C-arm or other adjustable, as well as stable, support 103. Examples of some components, which are often typically included in a basal member in mobile imaging systems, not all of which may be needed in some applications, such as various electronic systems, propulsion capabilities, controllers, power supply elements, displays and other portions that need not be directly incorporated into the support 103, are collectively grouped within dot-dashed outline 104.

An camera system 105, which may include optical imaging capabilities, provides illumination 106 via an optional illumination source 107, and may be attached to the support 103, or may be separate from the support 103, or may be absent, depending on the imaging task being addressed. The illumination source 107, when employed, is configured to provide a relatively even distribution of illumination 106, that is, to illuminate a field of view or a region, at a specified distance, or over a range of distances, from the illumination source 107. The illumination 106 may comprise full-spectrum illumination, bandwidth-controlled illumination, infrared illumination, ultraviolet illumination and/or other imaging illumination.

The illumination 106 and/or light from the region of interest gives rise to illumination 106', which returns to the camera system 105. One or more imaging devices or cameras 108, such as charge-coupled device-based, pixelated imaging apparatus configured to provide digital electronic signals representative of an image, may be postured to focus within a region that may be illuminated via the illumination source 107. In other words, the illumination source 107 is configured to provide a locus of evenly distributed light 106 over a spatial region that is coincident with a focal plane or field of view of the camera 108. In some applications, multiple cameras 108, for example providing different optical characteristics, may be contemporaneously employed. When stability and other mechanical support requirements warrant such, a counterweight 110 is coupled such that it is opposed to the camera 108.

The system 100 is configured to operate in conjunction with, or to include, a test subject support 111. In one embodiment, components of the system 100, and a test subject 112, are maintained in a defined geometric relationship to one another by the gantry, c-arm or other appropriate support 103. A distance between the camera system 105 and the patient 112 may be varied, depending on the type of examination sought, and the angle of the illumination 106 respective to the test subject 112 can be adjusted with respect to the body to be imaged 112, responsive to the nature of imaging desired. For example, a region of interest 116 may be postured to coincide with the focal plane of the camera system 105.

The gantry 102 or C-arm 103 and the test subject support or table 110 cooperatively engage to enable relative motion of the test subject 112 longitudinally, that is, along an axis extending into and out of the plane of FIG. 1. For example, when the system 100 is configured as a mobile or wheeled unit, the gantry, support or c-arm maybe be translated along an axis parallel to, for example, a long axis of the test subject support 111.

The system 100 also optionally includes a control module 120. The control module 120 may include a motor controller 122 configured to move the test subject support 111 and thus the test subject 112 relative to the illumination source 107 and/or support 103, and may also control motors in the gantry 102, C-arm or other support 103 or other device, and/or operate to position/move the camera system 105 relative to the test subject 112 and/or the rigid support 103.

The control module 120 may also include a drive controller 124 configured to control electrical drive parameters, for example affecting optical aspects and/or motion, delivered to the camera system 105.

In one embodiment, a chiller 128 supplies coolant to the camera system 105. The chiller 128 may be contained in a basal member comprising a mobile, self-propelled, internally powered, wheeled unit that also forms a base for cantilevering the support 103 and camera system 105 relative to the test subject support 110.

One or more computers 130 are connected to the control module 120 via a bus 132 configured for receiving data descriptive of operating conditions and configurations and for supplying appropriate control signals. Buses 134 and 134' act to transfer data and control signals, for example with respect to an image processing module 135, via interconnections such as 134', 134" that are configured for exchange of signals and data to and/or from the computer 130 as well as other elements of the system 100 and/or external computation or communications resources.

The system 100 also includes a bus 136, a bus 138 and an operator console 140. The operator console 140 is coupled to the system 100 through the bus 134. The operator console 140 includes one or more displays 142 and a user input interface 144. The user input interface 144 may include a keyboard, touchscreen, mouse or other tactile input device, and/or capability for voice commands and/or other input devices. The one or more displays 142 provide video, symbolic and/or audio or other information relative to operation of system 100, displaying user-selectable options and images descriptive of the test subject 112, and may display a user interface for facilitating user selection among various modes of operation and other system settings. The one or more displays 142 may be attached to the system 100, or may include display capability remote from the system 100.

The image processing module 135 facilitates automation of accurate measurement and assessment, and is capable of forming multiple, coordinated images for display, for example via the displays 142. The image processing module 135 may comprise a separate and distinct module, which may include application-specific integrated circuitry, or may comprise one or more processors coupled with suitable computer-readable program modules, or may comprise a portion of the computer 130 or other computation device.

The system 100 also includes data communications, storage and memory devices 150, coupled via the bus 136 to the computer 130 through suitable interfaces. The data communications, storage and memory devices 150 may include interface capabilities 152 for data exchange. The interface capabilities 152 may include RF, ultrasonic, infrared, fiber optic, cable and/or other data transmission/reception facilities, and may be broad-band, high data rate links for rapidly coupling larger amounts of data, such as still or moving images or volumetric data, between one or more computers or facilities. The data communications, storage and memory devices 150 may include mass data storage capabilities 154 and one or more removable data storage device ports 156. The one or more removable data storage device ports 156 are adapted to detachably couple to portable data memories 158, which may include optical, magnetic and/or semiconductor memories and may have read and/or write capabilities, and which may be volatile or non-volatile devices or may include a combination of the preceding capabilities.

For example, medical image data or data related to medical images may be transferred, stored or read, using conventional protocols via the various data communications, storage and memory devices 150. The Digital Imaging and Communications in Medicine or DICOM® protocol is one example of a conventional and widely-adopted data format which thus promotes sharing and transmission of digital medical image data, however, it will be appreciated that other data compression, decompression, transmission and interpretation protocols may be usefully employed.

The system 100 further includes an image data acquisition and conditioning module 160 having data inputs coupled to the camera system 105 and is also coupled by the bus 138 to the one or more computers 130. The data acquisition and conditioning module 160 includes circuitry for capturing digital data from the camera system 105 to be supplied to the one or more computers 130 for ultimate display via at least one of the displays 142 and for potential storage in the mass storage device 154 and/or data exchange with remote facilities (not shown in FIG. 1). The acquired image data may be conditioned in the data acquisition and conditioning module 160, the image processing module 135, the one or more computers 130, or a combination thereof.

The system 100 also includes a power supply 170, coupled via interconnections represented as a power supply bus 172, shown in dashed outline, to other system elements, and a power supply controller 174. The full range of interconnection of the power supply 170 to other elements of the system 100 is not shown in FIG. 1, in order to promote simplicity of illustration and ease of understanding.

In some embodiments, the system 100 is configured to be a mobile system equipped and includes portable power supply capabilities 170, such as a gang of batteries. In other words, the system 100 may comprise a wheeled unit and may be electromotively powered in self-contained fashion, lending physical agility to the ensemble of attributes offered by the system 100. The batteries, in turn, may provide a counterweight, facilitating cantilevering of the articulated mounting and positioning bracket 103 employed to support the camera system 105.

In some settings, such as in an emergency room, articulation of a mobility function may be limited to motion of a system 100 that is generally dedicated to application within that setting, suite or environment. In other settings, such mobility may include scheduled sequential visits to areas such as a cardiac unit, an ICU and other loci, where such imaging capability provides critical assistance, such as when the test subject 112 is not postured in a fashion consistent with movement of the test subject 112 and yet aperiodic variations in work load are not favorable to cost-effective deployment of a system 100 incapable of ready, self-propelled, operator-guided, "at need" physical translation of location. In one embodiment, electrically-powered motors coupled to a drive train effectuate operator-directed motion of the system 100.

Self-portable systems 100 employing a C-arm 103, rather than a gantry 102, also provide motion capabilities relative to the test subject 112 and promote maintaining some known spatial relationships between the camera system 105 and the test subject 112 while changing other spatial relationships therebetween. For example, a known distance between a region of interest may be maintained while engaging in an angular adjustment.

As part of initiating data collection, and then in the subsequent process of analyzing image data from the system 100, a clinician will need to interact with the system 100 in order to select an image type or mode, and to specify data manipulation and display aspects. Conversion of data from the camera 108 to diagnostically-useful image data includes specification of settings appropriate to the desired type of image and to aspects specific to the individual patient 112.

It is possible that the image processing may be executed on the same physical system that controls the illumination source 107 and other elements of the system 100 that collect the image data, and this may be desirable, for example, in the operating room. However, another manner in which this technique may be employed includes transfers, through physical or electronic media, of the image data from the system 100 to a remote computing device where the technique may be applied on the transferred data. This latter situation may apply with respect to diagnostic procedures, for example, where time is not of the essence, or to settings involving consultation with an expert who is not physically present, for comparison of "before and after" data and other types of considerations.

Features finding utility in one or more applications for optical imaging systems 100 include ease of transportation between areas, and suitable protection for the camera system 105 to avoid misalignment or damage which might occur during translation of the system 100 from one area of deployment to another. Capability for ready positioning of the camera system 105, coupled with physical stability when in position, also are useful aspects. For example, at least with some types of camera systems 105, it is helpful, in some applications, to be able to position the imaging device or camera 108 within a narrow focal range of the regions of interest, which may comprise patient tissue. In some applications, a range of about eighteen inches (forty-five centimeters) is useful.

In some applications, the support 103 needs to be able to position the camera system 105, weighing approximately 50 to 70 pounds (circa twenty to thirty kilograms). In some applications, the support 103 needs to be able to position the camera system 105, weighing about five to thirty pounds (two to twelve kilograms). The support 103 desirably includes capabilities for a broad range of motion, manual or motorized or both, ranging from three degrees of freedom of motion, to six or more degrees of freedom, as is described below in more detail with reference to FIGS. 6 and 7.

In at least one embodiment, the C-arm or other support 103 is movable in several directions along multiple image acquisition paths, including, for example, an orbital direction, a longitudinal direction, a lateral direction, a transverse direction, a pivotal direction and a "wig-wag" direction. In at least one embodiment, the illumination source 107 and camera 108 are movably positioned on the support 103. Thus, the support 103, along with the illumination source 107 and camera 108, may be moved and positioned about the positioning device 111 on, or in which, the patient or object being imaged 112 has been situated.

The displays or monitor/monitors 142 are usefully capable of accurately displaying high quality images and desirably are well positioned for surgeon visibility. Such displays 142 may include one or more of conventional flat-panel displays, projection-type displays, holographic displays or head-mounted displays.

In one embodiment, digital data representing images from the camera system 105 include DICOM-compatibility to promote interoperability, for example to enable data and image exchange in order to facilitate consultation between physicians, and for archiving image related data in a standardized, broadly-used format. Some types of illumination sources 107 and/or cameras 108 may require cooling, internally contained within mobile examples of such camera system 105 and equipped in conformance with avoiding spread of dust and other contaminants in a sterile environment. Motorized positioning of the camera 108 operable via remote control, such as tactile input devices or voice-actuated commands, may be desirable, for example, to enable a physician to position the camera 108 from the tableside.

There are many different ways possible for achieving articulated visual image apparatus other benefits of the subject matter disclosed herein. The apparatus of FIGS. 2 through 7, described below in more detail with reference to Section II, provide but a few examples for addressing these various needs.

II. Exemplary Mobile Support Systems and Articulation

Figure 4:
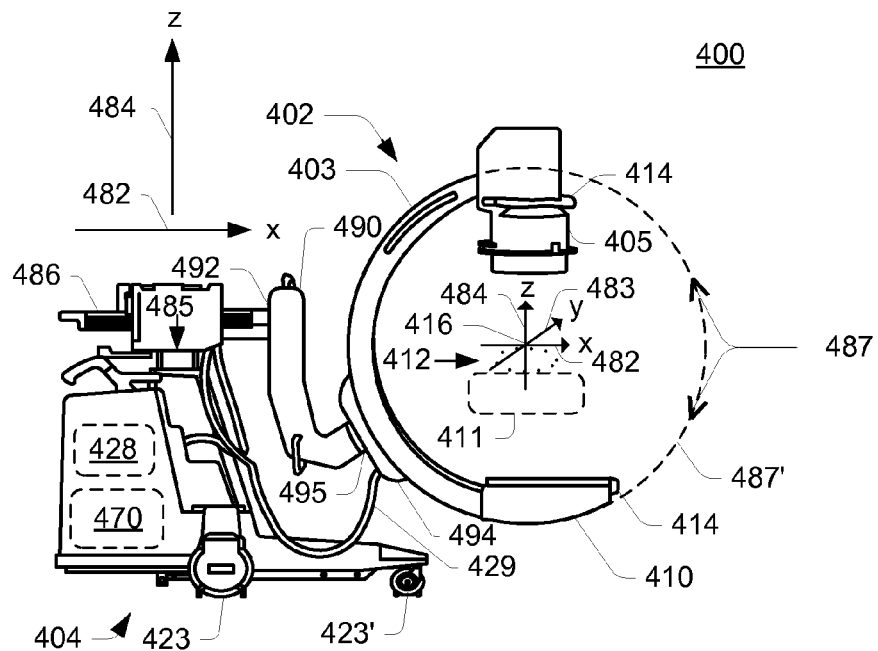
Figure 5:
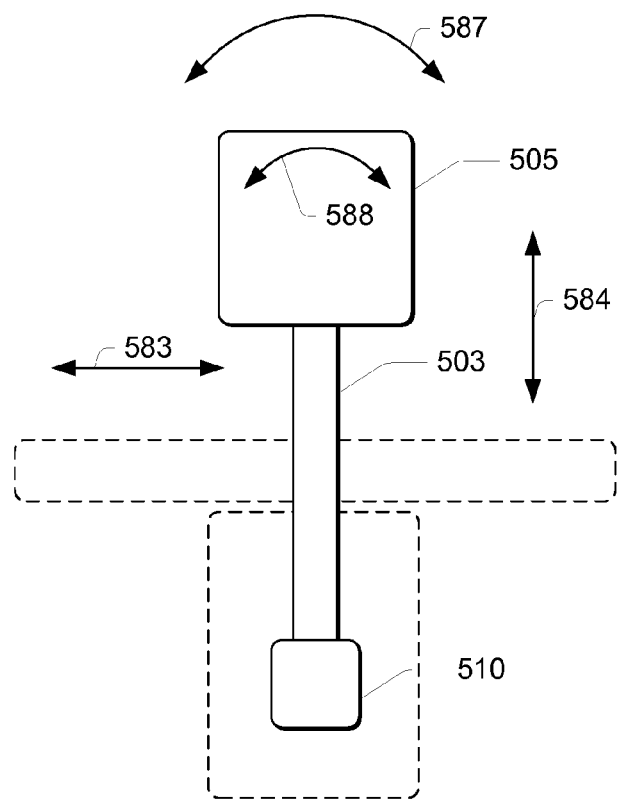
FIGS. 5 and 6 are simplified block diagrams illustrating a number of degrees of freedom of motion associated with the support systems of FIGS. 2 through 4.
Figure 6:
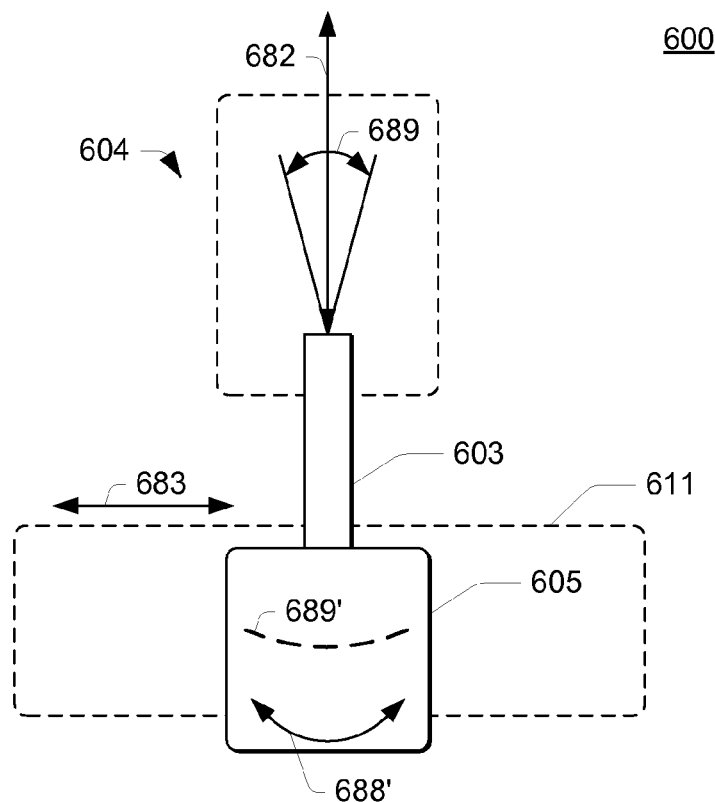
Figure 7:
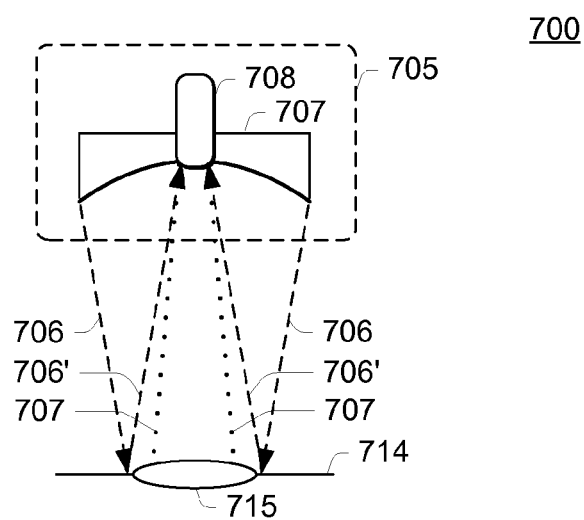
FIG. 7 is a simplified block diagram of an optical assembly capable of utility in the system of FIG. 1, which may be supported via apparatus, such as exemplified by the preceding FIGs.

FIGS. 2 through 5 illustrate simplified examples of support systems capable of utility in the system 100 of FIG. 1, while FIGS. 6 and 7 are simplified block diagrams illustrating a number of degrees of freedom of motion associated with the support systems of FIGS. 2 through 5. These support systems, and the optical imaging apparatus supported thereby, may find particular application in situations involving hospital operating rooms and emergency care areas, and in other medical arenas.

In general, imaging apparatus support systems are used in at least two different ways. In one mode of usage, the imaging device may be employed to render views all having a common patient-centric or isocentric aspect. In others, such as colonoscopic procedures, the field of view and the region being imaged need to be moved from one location to another, and one depth to another, in imaging the areas of interest. As a result, in some systems, either type of motion is enabled by the selection of suitable adjustments.

The support systems of FIGS. 2 through 5 illustrate examples employing modified mobile C-arm gantries as the imaging apparatus gantries, however, it will be appreciated that other types of support systems may be usefully employed, to provide one or more useful aspects such as mobility, appropriate degrees of freedom of motion and other properties, as described herein, without departing from the spirit and scope of the disclosed subject matter.

Figure 2:
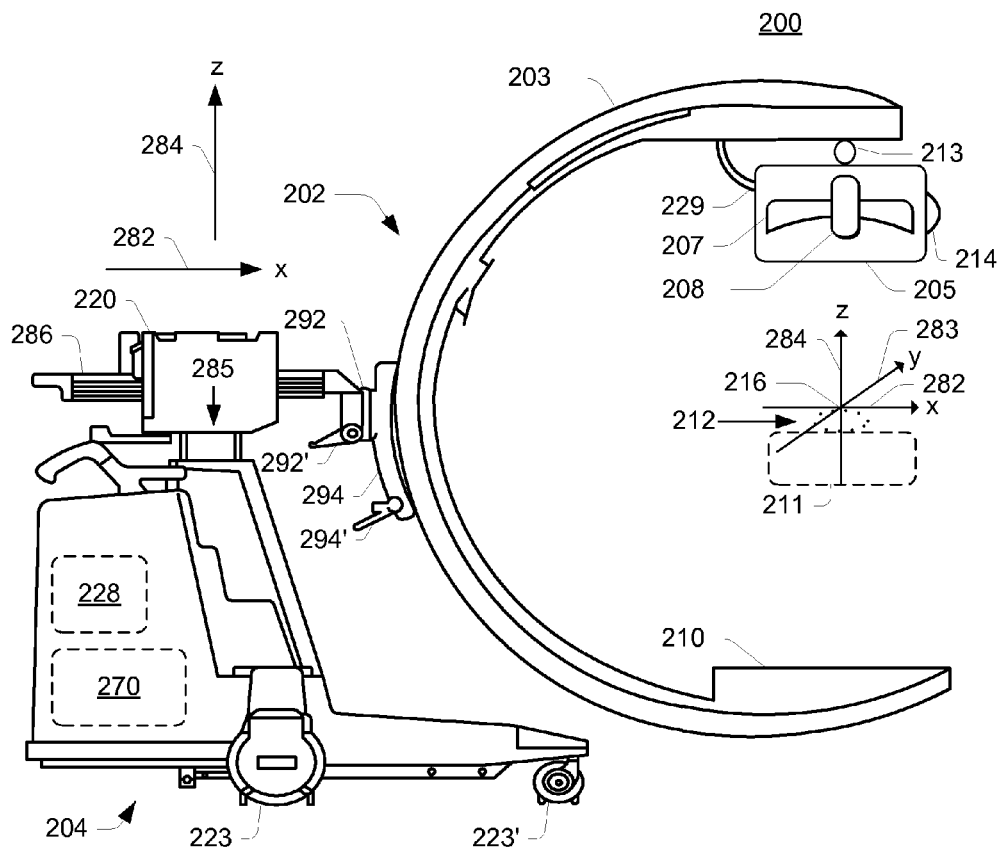
FIGS. 2 through 4 illustrate simplified examples of support systems capable of utility in the system of FIG. 1.

FIG. 2 illustrates an exemplary mobile imaging system 200. The mobile imaging system 200 includes an exemplary assembly of salient imaging components 202 providing a multi-axis profiling imaging capability that includes a rigid support 203, which is also adjustable, as is described in more detail below.

The support 203 of FIG. 2 is illustrated as comprising a rigid, arcuate member. A basal member or component support frame 204 that, in the example of FIG. 1, provides a pedestal for cantilevering the imaging components 202 and rigid support 203, and includes provisions, such as a modular 'drop-in' shielded electronics cabinet, for accommodating numerous infrastructural components, for example, such as are above described in conjunction with the dot-dashed outline 104 of FIG. 1.

An imaging apparatus 205, analogous to the camera system 105 of FIG. 1, is attached to the rigid support 203, which is illustrated as comprising a conventional c-arm support. The optical imaging apparatus 205 includes an illumination source 207 and one or more imaging devices, such as a camera 208.

A counterweight 210, if needed, may be provided, for example at an end of the c-arm 203 distal from, or other position associated with other forms or support and suitably positions relative to, the optical imaging assembly 205. As a result, balance and maneuverability of the resulting system 200 can similar to that of conventional mobile x-ray C-arm positioning devices, facilitating operator training by maintaining configuration and application similarities.

More specifically, in usage, an isocentric design postures a region of interest or tissue of interest at a desired focal length, while adjustments are made to effect changing an angle of the line-of-sight of the optical imaging apparatus 205. Conventional gas spring assists, which may reduce the weight requirement of the counterweight 210, maintain ease of manual positioning through at least a portion of those ranges of positions that are most important and most clinically beneficial, while allowing for locked positioning after adjustment.

A test subject support or operating table 211 is illustrated in dashed outline below the imaging apparatus 205. The test subject support 211 is illustrated in conjunction with a test subject 212, represented by a dotted elliptical outline.

An adjustable multi-axial mount 213, such as a gimbal or motorized, computer-regulated and/or operator controllable articulation, couples the imaging system 205 to the rigid support 203. A bumper 214 may be coupled to the imaging apparatus 205 to provide a measure of protection from physical shock, as will be discussed below in more detail.

The test subject 212 is postured to place a portion of the test subject 212 comprising a region of interest 216 in coincidence with a focal plane of the camera 208, via adjustment of the rigid support 203, the basal member 204, the test subject support 212 and/or the adjustable mount 213.

As a portion of the basal member 204, the mobile imaging system 200 may optionally include control module 220. Forward mobility for the system 200 may be effectuated by powered wheels 223, and casters 223' may provide directional maneuverability. In some embodiments, a chiller 228 provides chilled coolant via conduits 229. The conduits 229 are routed, in part, through a channel in the rigid support 203.

Electrical power for computer-controlled or operator-directed motors for driving a propulsion system (not illustrated) may be supplied via a self-contained power supply 270. In some embodiments, the power supply may comprise conventional lead-acid batteries positioned to counterbalance and cantilever the rigid support 203. As a result, the system 200 is able to provide functionality and/or mobility, even during a power outage.

Various degrees of translational and rotational freedom of motion are described with reference to an exemplary Cartesian coordinate system. FIG. 2 depicts x-axis 282, y-axis 283 and z-axis 284, collectively defining an origin, which is adjustable to be coincident with the region of interest 216. The origin also is coincident with a focal plane of camera 208 of the imaging apparatus 205. In this example, the focal plane is in the x-y plane.

User-directed control of motors for propelling the imaging system 200, and/or for actuating a motorized lift 285 for adjusting elevation of the imaging components 202, among other purposes, may be realized, for example via a tableside and/or other user input controls (not shown in FIG. 2) in data communication with, but physically separate or separable from, the rigid support 203 and/or the support frame 204. Control access points may also be included via the 'dog house' control module 220.

Hand-, foot-, and/or voice-operable input-output media (e.g., input media 144, FIG. 1) may provide controls for magnification modification, such as zoom in or out capabilities, for the camera 208, can trigger or manually over-ride automatic focus aspects, and may be used to select among functions such as snap or still image preparation, cine or movie-like displays, recall of image data from electronic or electronically-compatible image storage elements (e.g., memory devices 150 and/or data interface 152 of FIG. 1) for purposes of review, or to realize side-by-side comparison of different views, for suitably-weighted overlay of multiple imaging modes, such as fluorescence images overlaid with reflected illumination images, or for other comparisons, or for permitting multiple image data types to be contemporaneously engaged, or for changing the display 142 to modify or select color, black and white, functional optical, merge and controls for changing the relative weight of imaged components in forming composite images.

The motorized lift column 285 provides controlled z-axis 284 motion capabilities, and a cross-arm and brake assembly 286 provides controlled y-axis 283 motion. An articulated cross-arm rotation joint 292 and lock 292' allows 'propeller' rotation (also known as 'flip-flop' motion) of the rigid support 203, to put it into a desired position, and then locked. A rear-capture sliding joint 294 mechanically couples the basal member to the rigid support 203. The sliding joint 294 together with a mechanical lock 294' facilitates orbital rotation (rotation about the y-axis 283, that is, in the x-z plane) of the rigid support 203 and maintaining a desired position.

Figure 3:
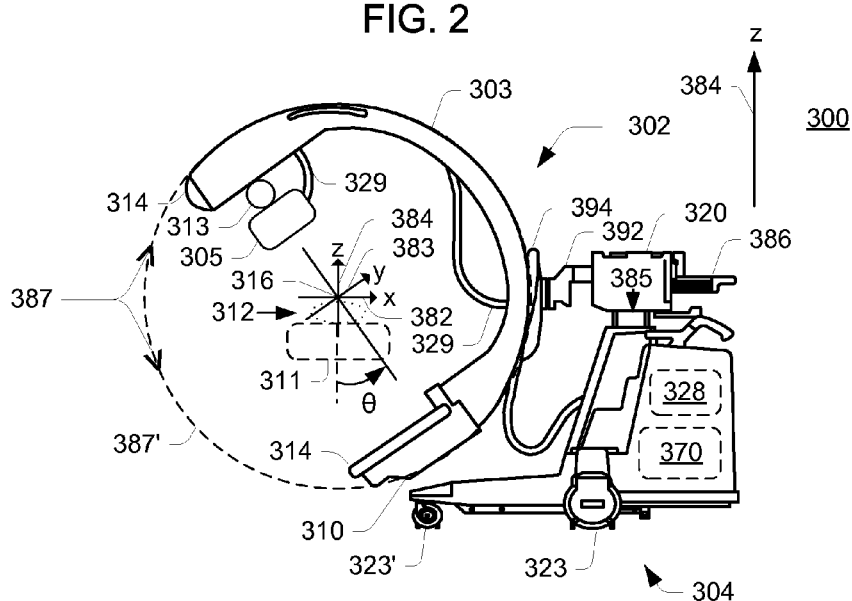

FIG. 3 depicts an exemplary mobile imaging system 300, in a different posture than that shown in FIG. 2. The rigid support 303 of FIG. 3 has been orbitally rotated (as indicated by direction arrows 387 and dashed circular outline 387') by an angle θ. As a result, an imaging axis 384' is tilted, relative to the z axis 384, isocentrically, that is, such that intersection of the focal plane of the imaging assembly 305 with the region of interest 316 is maintainable.

Additionally, the optical imaging assembly 305 of FIG. 3 is mounted such that the bumper 314 directly coupled the rigid support 303 and the rigid support protect the optical imaging assembly 305 from physical shock.

FIG. 4 illustrates another exemplary mobile imaging system 400. The system 400 incorporates a motorized lift column 485 for providing linear motion along the z axis 484, however, in contrast to the systems 200 and 300 of FIGS. 2 and 3, the cross-arm 486 couples to a conventional L-arm 490 via a cross arm lockable rotary joint 492.

The cross arm rotation and lock joint 492 permits so-called "propeller" type rotation of the rigid support 403. A rear capture channel 494 and associated lock provide orbital rotation capability, i.e., as shown by direction arrows 487, via another articulation 495 that is coupled to the L-arm 490. It will be appreciated that orientation, such as isocentric rotation, is possible via other types of mounting and articulation apparatus and shapes for the support systems. For example, such systems may be designed to allow rotation within a predetermined subset of, or throughout, the 360 degrees of possible orientations.

FIG. 5 is a simplified block diagram showing a front view (i.e., looking to the left or down the x-axis 482 depicted in FIG. 4) of a mobile imaging system 500, illustrating several modes of articulation. The system 500 of FIG. 5 includes representations of the rigid support 503, the basal member 504 (in dashed outline), the imaging apparatus 505, the counterweight 510 and the patient support table 511 (in dashed outline). A y-axis 583 direction arrow and a z-axis direction arrow 584 facilitate relating the geometry of FIG. 5 to that of other FIGs.

A bidirectional arrowed arc 587 indicates a 'propeller' type motion, corresponding, for example, to adjustment as described with reference to slidable coupling 292 of FIG. 2, or rotation about the cross-arm rotary joint 492 of FIG. 4. The propeller motion may be isocentric.

In other words, when the initial alignment of the imaging system 500 is such that the region of interest (such as region 416) coincides with a center about which the rotation or propeller motion occurs, the region of interest is separated from the imaging apparatus 505 by a constant distance, which is chosen such that the focal plane of the imaging apparatus 505 intersects the region of interest. Consequently, rotation of the rigid support 503 via propeller motion need not necessarily require other positional adjustments or optical adjustments to maintain image integrity.

A bidirectional arrowed arc 588 indicates a different type of angular adjustment of the imaging apparatus 505 relative to the rigid support 503. The arc 588 may correspond to adjustment of the imaging 505 apparatus via the gimbal-type arrangement mentioned with respect to FIGS. 2 and 3. This form of articulation does not tend to be isocentric, and thus may be coordinated with adjustments in order to maintain focus or to continue to image the region of interest.

FIG. 6 is a simplified block diagram showing a top plan view (i.e., looking to the down the z-axis 484 depicted in FIG. 4) of a mobile imaging system 600, illustrating several modes of articulation. The rendering of FIG. 6 includes representations of the rigid support 603, the basal member 604 (in dashed outline), the imaging apparatus 605 and the patient support table 611 (in dashed outline). An x-axis direction arrow 682 and a y-axis 683 direction arrow facilitate relating the geometry of FIG. 6 to that of other FIGs.

A bidirectional arrowed arc 688' indicates a rotation of the optical imaging assembly 605 about a center 688", for example, based on articulation of a joint such as the gimbal 313 of FIG. 3. However, in practice, this type of image rotation is easily accomplished without need for physical motion, for example, via the image processing engine 135 of FIG. 1. A bidirectional arrowed arc 689 indicates a 'wig-wag' type of articulation. The effect of this type of adjustment is to sweep the focus of the imaging system 605 along an arc 689', represented by a dashed arc in FIG. 6. This type of motion typically has very limited range of rotation for the rigid support about a center 689".

Usage of a platform, such as briefly described with reference to FIGS. 2 through 6, for deployment of imaging apparatus, provides benefits. Both types of systems may use similar optical displays, such as dual flat-panel monitors capable of providing high quality color or black-and-white images, and readily mountable to provide position adjustability, for example via an articulating arm assembly. As a result, parts inventories, maintenance, and operator training aspects provide a degree of synergism, resulting in reduced overhead.

The disclosed examples can provide mass and positioning flexibility aspects similar to those of conventional mobile x-ray systems. The 'footprint' and mobility aspects for such systems are 'tried and true' in the operating room context, and are compatible with the optical system requirements. The following section briefly describes some exemplary optical imaging assembly considerations.

III. Optical Imaging Assembly

In the previous section, tools developed in furtherance of functionality with respect to mobile imaging apparatus were disclosed and described. In this section, an optical imaging assembly, and description of capabilities of the imaging assembly, are provided with reference to a block diagram. FIG. 7 is a simplified block diagram of an optical system 700 capable of utility in the system 100 of FIG. 1, and which may be supported via apparatus such as exemplified by FIGS. 2 through 6.

The imaging assembly 705 includes an suitable light beam 706 via an illumination source 707, and also includes a camera 708. The camera 708 has a focal plane 714, and is focused to be able to accurately image features within a region 715. In some embodiments, the illumination source 707 provides a light beam 706 having intensity and spectral characteristics selected for a particular type of imaging task.

The illumination source 707 and camera system 708 are selected to be able to provide images based on illumination 706' leaving the region of interest, which may have wavelength characteristics corresponding to a selected band of optical frequencies falling within a range extending from the infrared, that is, a wavelength of up to one point three microns, to the ultraviolet. In some instances, the excitation illumination 706 may be chosen to have a wavelength which excites fluorescence, based on the endogenous properties of the tissues being imaged, or based on specific compounds introduced into the patient.

Figure 8:
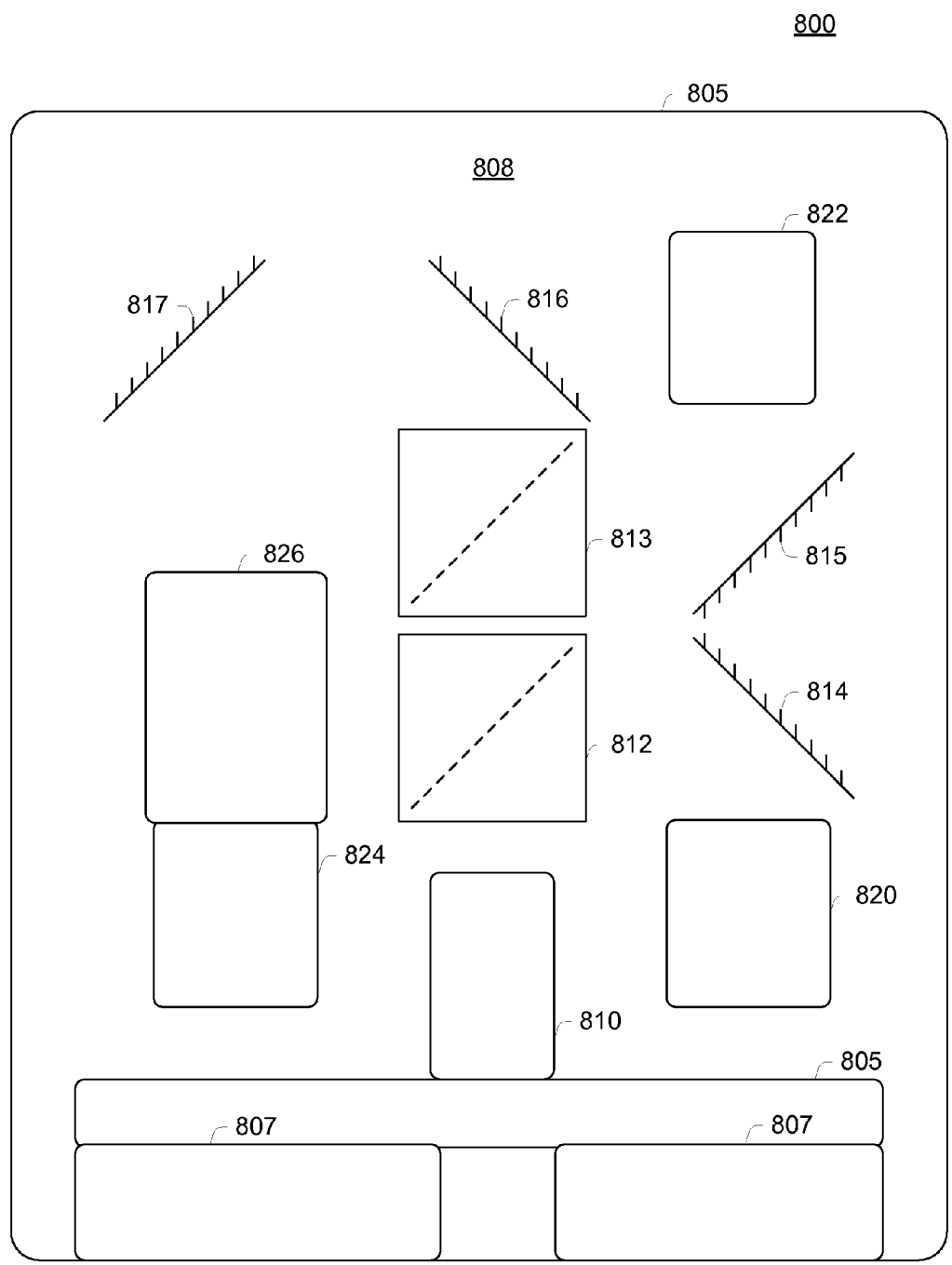
FIG. 8 is a simplified block diagram of an optical assembly embodiment capable of utility in the system of FIG. 1.

FIG. 8 is a simplified block diagram of an embodiment 800 of an optical assembly 805 capable of utility in the system of FIG. 1. The optical assembly 805 of the embodiment 800 includes a transparent cooling plate 805 and a cold light source 807, such as an LED light source, mounted in front of the transparent cooling plate 805. A lens and focusing assembly 810, which may be motor-driven and controllable via the computer 130 and/or the user input media 144 of FIG. 1, is configured on a side of the cooling plate 805 opposite an opening extending through the light source 807. A first dichroic beam splitter/filter 812 is positioned in an optical path at an output of the lens assembly 810, and a second dichroic beam splitter/filter 813 is positions in the optical path at one output of the first dichroic beam splitter/filter 812.

Mirrors (which may be formed as prisms or in other conventional ways) 814, 815, 816 and 817 are each positioned in respective portions of the optical paths resulting from the first 812 and second 813 beam splitters. An optical color video camera 820 is positioned to capture the portion of the incident light reflected by the first mirror 814. A near infrared camera 822 is positioned to capture the portion of the incident light reflected by the second mirror 815. A third near infrared camera 824 is positioned to capture light reflected by the third and fourth mirrors 816, 817, after amplification by an optical image intensifier 826.

In one embodiment, the optical video camera 820 is a conventional CCD-type camera, such as a model IMC-80F camera manufactured by Imi Tech of Seoul, Korea and distributed by Graftek Imaging of Austin, Tex.

In one embodiment, the near infrared cameras 822 and 824 are monochrome cameras, such as a C4742-80-12AG camera, manufactured by Hamamatsu Photonics K.K. having facilities throughout Japan and also distributed by Graftek Imaging. Filters such as may be incorporated with the dichroic beam splitter 813, or at an input to each camera 822, 824, or both, may, for example, direct 700 nanometer light to the camera 824 and 800 nanometer light to the camera 826.

Fluorinert® coolant, or other fluid coolant that is relatively transparent to the illumination for the images formed from the cameras 820, 822 and 824 is circulated through the cooling plate 805. This provides chilling, if needed, for the cameras 822/824, and thermally isolates the camera system from the light source 807.

IV. Hardware and Operating Environment

Figure 9:
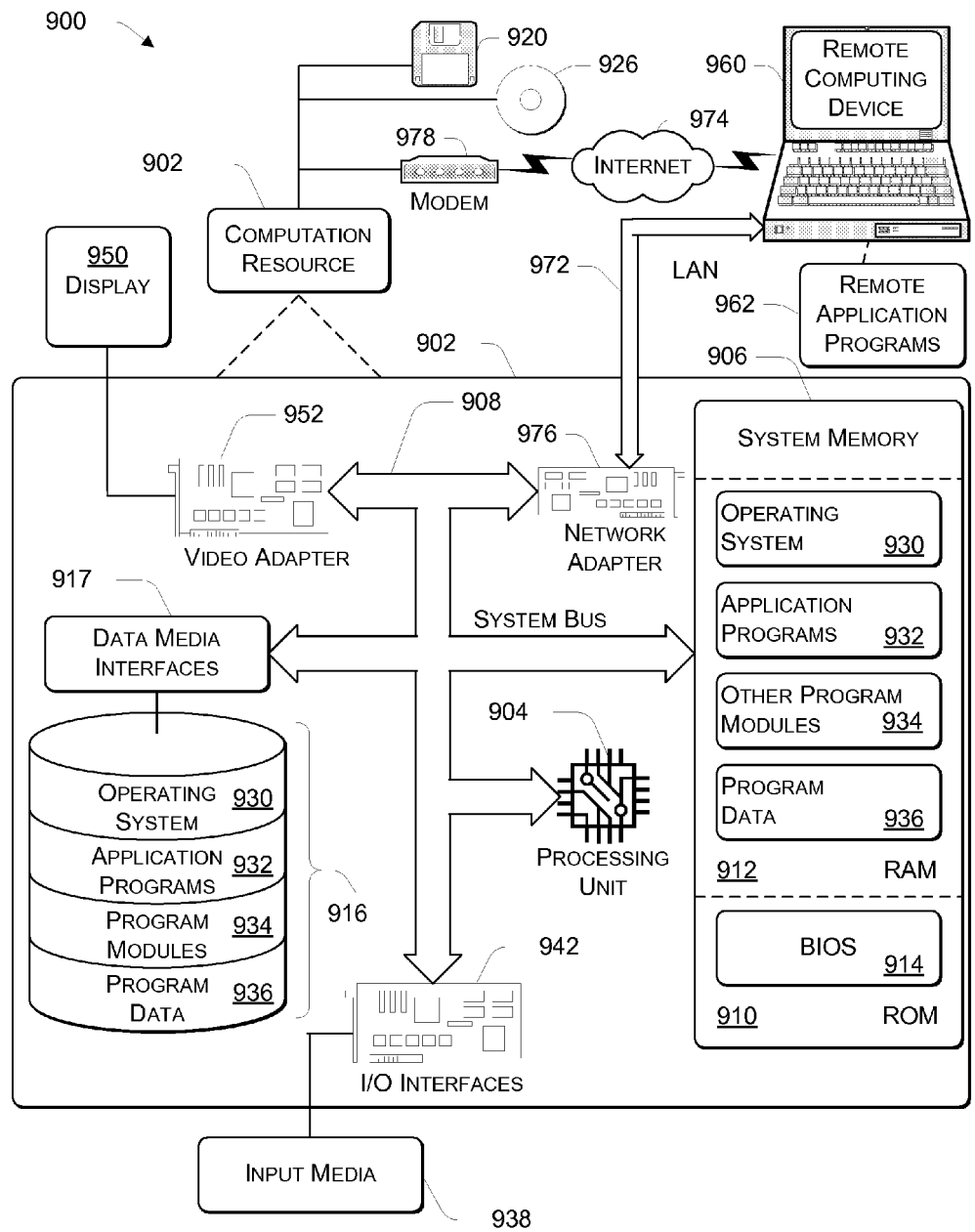
FIG. 9 illustrates an example of a general computation resource useful in the context of the environment of FIG. 1.

FIG. 9 illustrates an example of a general computer environment 900 that includes a computation resource 902 capable of implementing the processes described herein. It will be appreciated that other devices may alternatively used that include more components, or fewer components, than those illustrated in FIG. 9.

The illustrated operating environment 900 is only one example of a suitable operating environment, and the example described with reference to FIG. 9 is not intended to suggest any limitation as to the scope of use or functionality of the embodiments of this disclosure. Other well-known computing systems, environments, and/or configurations may be suitable for implementation and/or application of the subject matter disclosed herein.

The computation resource 902 includes one or more processors or processing units 904, a system memory 906, and a bus 908 that couples various system components including the system memory 906 to processor(s) 904 and other elements in the environment 900. The bus 908 represents one or more of any of several types of bus structures, including a memory bus or memory controller, a peripheral bus, an accelerated graphics port and a processor or local bus using any of a variety of bus architectures, and may be compatible with SCSI (small computer system interconnect), or other conventional bus architectures and protocols.

The system memory 906 includes nonvolatile read-only memory (ROM) 910 and random access memory (RAM) 912, which may or may not include volatile memory elements. A basic input/output system (BIOS) 914, containing the elementary routines that help to transfer information between elements within computation resource 902 and with external items, typically invoked into operating memory during start-up, is stored in ROM 910.

The computation resource 902 further may include a non-volatile read/write memory 916, represented in FIG. 9 as a hard disk drive, coupled to bus 908 via a data media interface 917 (e.g., a SCSI, ATA, or other type of interface); a magnetic disk drive (not shown) for reading from, and/or writing to, a removable magnetic disk 920 and an optical disk drive (not shown) for reading from, and/or writing to, a removable optical disk 926 such as a CD, DVD, or other optical media.

The non-volatile read/write memory 916 and associated computer-readable media provide nonvolatile storage of computer-readable instructions, data structures, program modules and other data for the computation resource 902. Although the exemplary environment 900 is described herein as employing a non-volatile read/write memory 916, a removable magnetic disk 920 and a removable optical disk 926, it will be appreciated by those skilled in the art that other types of computer-readable media which can store data that is accessible by a computer, such as magnetic cassettes, FLASH memory cards, random access memories (RAMs), read only memories (ROM), and the like, may also be used in the exemplary operating environment.

A number of program modules may be stored via the non-volatile read/write memory 916, magnetic disk 920, optical disk 926, ROM 910, or RAM 912, including an operating system 930, one or more application programs 932, other program modules 934 and program data 936. Examples of computer operating systems conventionally employed for some types of three-dimensional and/or two-dimensional medical image data include the NUCLEUS® operating system, the LINUX® operating system, and others, for example, providing capability for supporting application programs 932 using, for example, code modules written in the C++® computer programming language.

A user may enter commands and information into computation resource 902 through input devices such as input media 938 (e.g., keyboard/keypad, tactile input or pointing device, mouse, foot-operated switching apparatus, joystick, touchscreen or touchpad, microphone, antenna etc.). Such input devices 938 are coupled to the processing unit 904 through a conventional input/output interface 942 that is, in turn, coupled to the system bus. A monitor 950 or other type of display device is also coupled to the system bus 908 via an interface, such as a video adapter 952.

The computation resource 902 may include capability for operating in a networked environment (as illustrated in FIG. 1, for example) using logical connections to one or more remote computers, such as a remote computer 960. The remote computer 960 may be a personal computer, a server, a router, a network PC, a peer device or other common network node, and typically includes many or all of the elements described above relative to the computation resource 902. In a networked environment, program modules depicted relative to the computation resource 902, or portions thereof, may be stored in a remote memory storage device such as may be associated with the remote computer 960. By way of example, remote application programs 962 reside on a memory device of the remote computer 960. The logical connections represented in FIG. 9 may include interface capabilities, e.g., such as interface capabilities 152 (FIG. 1) a storage area network (SAN, not illustrated in FIG. 9), local area network (LAN) 972 and/or a wide area network (WAN) 974, but may also include other networks.

Such networking environments are commonplace in modern computer systems, and in association with intranets and the Internet. In certain embodiments, the computation resource 902 executes an Internet Web browser program (which may optionally be integrated into the operating system 930), such as the "Internet Explorer®" Web browser manufactured and distributed by the Microsoft Corporation of Redmond, Wash.

When used in a LAN-coupled environment, the computation resource 902 communicates with or through the local area network 972 via a network interface or adapter 976. When used in a WAN-coupled environment, the computation resource 902 typically includes interfaces, such as a modem 978, or other apparatus, for establishing communications with or through the WAN 974, such as the Internet. The modem 978, which may be internal or external, is coupled to the system bus 908 via a serial port interface.

In a networked environment, program modules depicted relative to the computation resource 902, or portions thereof, may be stored in remote memory apparatus. It will be appreciated that the network connections shown are exemplary, and other means of establishing a communications link between various computer systems and elements may be used.

A user of a computer may operate in a networked environment 100 using logical connections to one or more remote computers, such as a remote computer 960, which may be a personal computer, a server, a router, a network PC, a peer device or other common network node. Typically, a remote computer 960 includes many or all of the elements described above relative to the computer 900 of FIG. 9.

The computation resource 902 typically includes at least some form of computer-readable media. Computer-readable media may be any available media that can be accessed by the computation resource 902. By way of example, and not limitation, computer-readable media may comprise computer storage media and communication media.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic storage devices, or any other media which can be used to store computer-intelligible information and which can be accessed by the computation resource 902.

Communication media typically embodies computer-readable instructions, data structures, program modules or other data, represented via, and determinable from, a modulated data signal, such as a carrier wave or other transport mechanism, and includes any information delivery media. The term "modulated data signal" means a signal that has one or more of its characteristics set or changed in such a manner as to encode information in the signal in a fashion amenable to computer interpretation.

By way of example, and not limitation, communication media include wired media, such as wired network or direct-wired connections, and wireless media, such as acoustic, RF, infrared and other wireless media. The scope of the term computer-readable media includes combinations of any of the above.

The computer 902 may function as one or more of the control segments of module 120 (FIG. 1), the computer 130, the operator console 140 and/or the data acquisition and conditioning module 160.

V. CONCLUSION

The disclosed examples combine a number of useful features and present advantages in modern hospital settings. These examples leverage prior capabilities associated with mobile x-ray imaging tools, including mechanical and electrical reliability under a wide range of potentially-applicable circumstances. Additionally, compatibility with existing tools and modes for image data representation, and conventional image data storage and exchange standards facilitate interoperability with existing modules developed for those purposes, as well as promoting compatibility with newer approaches, such as integrated surgical navigation. The disclosed capabilities also benefit from compatibility with existing systems, and thus coordinate with other operator training, reducing probability of error, such as may occur in time-critical scenarios.

These examples additionally employ tools for remote, table-side positioning, in fashions often familiar to many physicians from prior experience with other mobile medical imaging tools, such as mobile fluoroscopic tools employed in contexts including cardiac surgery. Combining surgical navigation sensors with motorized, operator-directed imaging tool motion enhances a gamut of opportunities for automated positioning solutions. Maintaining broad compatibility with requirements for ancillary elements needed in the surgical environment, such as cart draping accessories and c-arm or other gantry or support mechanism draping, reduces the breadth of inventory items needed for infrastructural elements, presenting cost and supply management benefits, and aiding in appropriate deployment of those types of items in usage.

Although specific embodiments have been illustrated and described herein, it will be appreciated by those of ordinary skill in the art that any arrangement which is calculated to achieve the same purpose may be substituted for the specific embodiments shown. This disclosure is intended to cover any adaptations or variations. For example, although described in procedural terms, one of ordinary skill in the art will appreciate that implementations can be made in a procedural design environment or any other design environment that provides the required relationships.

In particular, one of skill in the art will readily appreciate that the names or labels of the processes and apparatus are not intended to limit embodiments. Furthermore, additional processes and apparatus can be added to the components, functions can be rearranged among the components, and new components to correspond to future enhancements and physical devices used in embodiments can be introduced without departing from the scope of embodiments. One of skill in the art will readily recognize that embodiments are applicable to future communication devices, different file systems, and new data types. The terminology used in this disclosure is meant to include all object-oriented, database and communication environments and alternate technologies which provide the same functionality as described herein.

What is claimed is:

1. A camera support comprising:
   a rigid member;
   an illumination source rotatably mounted on a rigid member;
   a camera system mounted on the rigid member and coupled to the illumination source;
   a group of guides having mutually orthogonal axes of motion, at least one of the guides including a computer-controllable motor drive for lifting the rigid member;
   a group of joints each contributing a degree of freedom of rotation to the rigid member; and
   a basal member coupled to the rigid member via the group of guides and the group joints, the rigid member being cantilevered thereby, the group of guides and the group of joints cooperatively engaging to adjust a position of the camera system to cause a focal plane to coincide with a region of interest and to facilitate motion of the camera system while maintaining the focal plane in coincidence with the region of interest.

2. The camera support of claim 1, further comprising:
   a controller;
   multiple motor drives, each coupled to at least one of the group of guides and the group of joints;
   a command input device coupled to the controller and conveying operator commands to the controller to cause controlled motion of the camera system responsive to operator commands via at least one of the multiple motor drives.

3. The camera support of claim 1, further comprising:
   a controller;
   multiple motor drives, each coupled to at least one of: the group of guides and the group of joints;
   a tactile command input device coupled to the controller and conveying operator commands to the controller to cause controlled motion of the camera system responsive to operator commands via at least one of the multiple motor drives.

4. The camera support of claim 1, wherein the camera system and illumination source form an optical imaging system, the optical imaging system providing a digitized image based on image data represented by light in a range extending from infrared to ultraviolet.

5. The camera support of claim 1, wherein the group of joints each contribute to at least one degree of freedom of rotation chosen from a group consisting of: wig-wag, flip-flop, tilt and orbital motion.

6. The camera support of claim 1 wherein the rigid member further comprises an arcuate member slidably coupled to a collar to permit orbital rotation of the rigid member about the isocenter.

7. A mobile optical imaging system comprising:
   an optical imaging apparatus coupled to one end of an arcuate supporting member, the optical imaging apparatus including an illumination source and a camera system, the camera system providing a digital signal representing an image;
   a first counterweight coupled to another end of the arcuate supporting member distal from the one end, the first counterweight being opposed to the optical imaging apparatus;
   a basal member providing a second counterweight for cantilevering the arcuate support member, the basal member including a self-contained power supply and motorized propulsion capabilities, the arcuate member being slidably coupled to the basal member to permit rotation of the optical imaging apparatus and the first counterweight about an isocenter coincident with a focal plane of the optical imaging assembly.

8. The mobile optical imaging system of claim 7, wherein the basal member and the arcuate supporting member cooperatively provide:
   linear translation capability for positioning the isocenter to be coincident with a region of interest, the linear translation capability providing controlled linear motion along three orthogonal linear axes; and
   multiple rotational articulation capabilities configured to permit adjustment of the optical imaging apparatus about the region of interest while maintaining the isocenter in coincidence with the region of interest.

9. The mobile optical imaging system of claim 7, further comprising:
   a controller;
   multiple motor drives each coupled to at least one of a group of guides configured to provide linear translation capabilities in three dimensions;
   multiple rotational controllers each coupled to at least one of articulations providing a degree of rotational freedom, and collectively providing at least three degrees of freedom; and
   a tactile command input device coupled to the controller and conveying operator commands to the controller to cause controlled motion of the optical imaging apparatus responsive to operator commands via the multiple motor drives and multiple rotational controllers.

10. The mobile optical imaging system of claim 7, further comprising a chiller supplying chilled coolant to the optical imaging apparatus through a channel formed in the arcuate member.

11. The mobile optical imaging system of claim 7, further comprising one or more displays capable of rendering images from the electronic data and of functioning as a touch-screen for providing control functions.

12. The mobile optical imaging system of claim 7, further including a tableside remote control, along with tactile or other user-directed controls, configured to provide optical effects from the optical imaging assembly and a data conditioning module including: rotation of the image on a display, zoom in-out, auto focus, snap, cine, recall/review, changing display between color, functional optical, merge and controls for changing relative strength of the overlaid information and the basic image data.

13. The mobile optical imaging system of claim 7, further including: a data conditioning module capable of processing the digital signal to provide a modified signal representing a desired image type.

14. The mobile optical imaging system of claim 13, further including:
   a display coupled to the data conditioning module, the display being configured to provide an optical image based on the modified signal.

* * * * *